Nov. 18, 1969 J. J. PONCHALEK Plant Pat. 2,941
PEACH TREE
Filed March 8, 1968
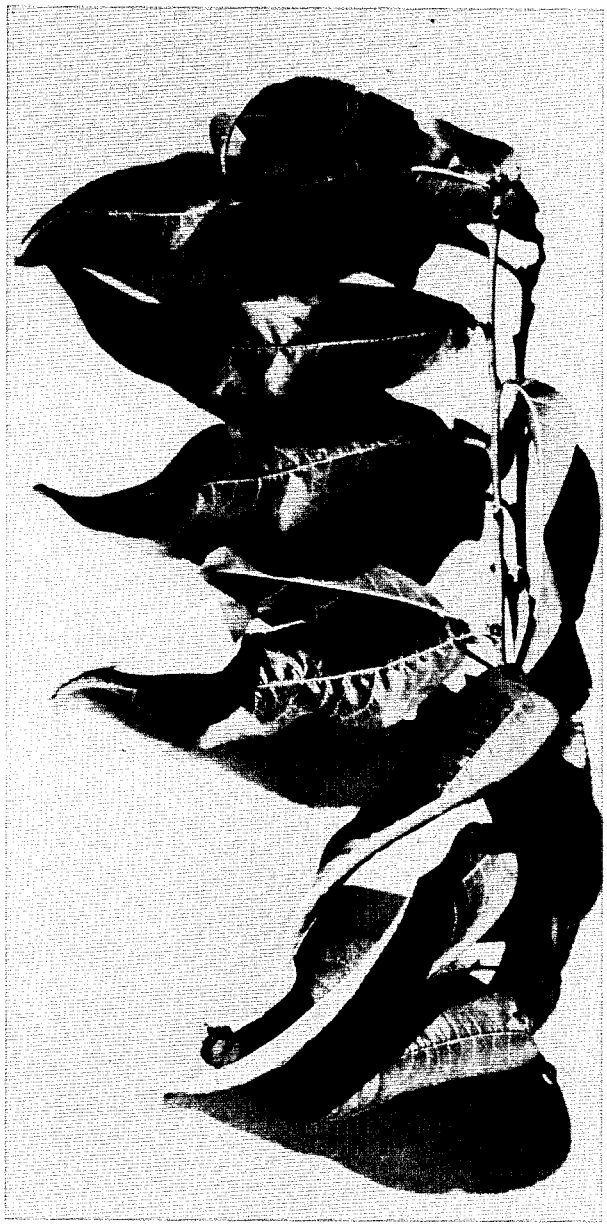
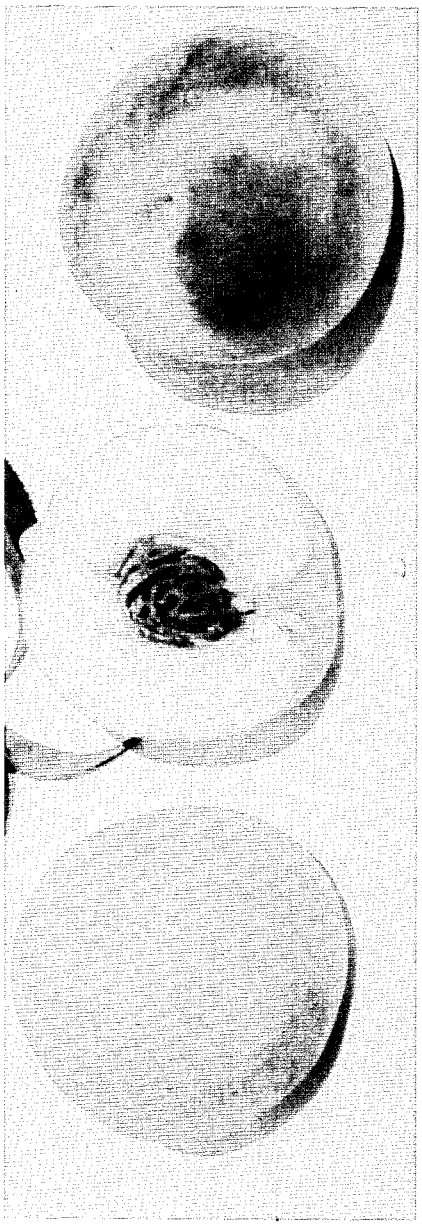
Inventor.
J. J. Ponchalek
By: Robbins & Robb
Attorneys.

United States Patent Office

Plant Pat. 2,941
Patented Nov. 18, 1969

2,941
PEACH TREE

Joseph J. Ponchalek, Ithaca, N.Y., assignor to Stark Bro's Nurseries & Orchards Company, Louisiana, Mo., a corporation of Missouri

Filed Mar. 8, 1968, Ser. No. 711,814
Int. Cl. A01h *5/08*
U.S. Cl. Plt.—43 1 Claim

The present invention relates to a new and distinct variety of peach tree of the yellow-fleshed, freestone, fruit-bearing type, which was originated by me from a large number of peach pits of unknown parentage planted by me in a trial plot in my orchard situated in the town of Danby, Tompkins County, N.Y.

After continuously observing the trial plot of seedlings, referred to above, over a prolonged period of years (I selected this particular seedling as having improved characteristics which would be commercially valuable, and I carefully preserved the new seedling and took steps to have it asexually reproduced by budding as performed on my behalf by my assignee in Pike County, Ill. Continued observations and tests of the original seedling and the progeny thereof derived by budding as aforesaid, fully confirmed and convinced me that it represents a new and distinct variety of superior commercial value, as evidenced by the following unique combination of characteristics which are outstanding in the new variety and which distinguish it from all other peach varieties of which I am aware:

(1) A hardy tree and flower bud habit;

(2) A fruit ripening season about the same as the Gleason strain of "Early Elberta" (unpatented), but the fruit skin being a much deeper red color which develops about a week before maturity to enable earlier harvesting and shipping;

(3) A deeper yellow fruit flesh color; and (4) A richer and sweeter fruit flavor.

Asexual reproduction of my new variety by budding shows that the foregoing charatceristics and distinctions come true to form and are established and transmissible through succeeding propagations.

The accompanying drawing shows typical specimens of the fruit and foliage of my new variety as depicted in color as nearly true as it is reasonably possible to make the same in a color illustration of this character, said fruit specimens being shown in elevation, as well as in cross section.

The following is a detailed description of my new variety, with color terminology in accordance with Ridgway's Color Standards and Nomenclature (hereinafter abbreviated as (R), Munsell Color Chart (hereinafter abbreviated as (M)), and the Horticultural Colour Guide (hereinafter abbreviated as (HCG)), as indicated, except where general color terms of ordinary dictionary significance are obvious, and based upon observations made from specimens grown in Pike County, Ill.:

Dates of first and last pickings: About Aug. 17 and Aug. 21, respectively.

Tree: Medium large; vigorous; spreading; vase-formed; hardy; productive; regular bearer.

*Trunk.*—Medium stockiness.

*Branches.*—Medium slender; smooth; glossy.

*Color.*—Victoria Lake, Plate I, Color 1, Tone M (R).

*Lenticels.*—Numerous; medium small.

*Leaves.*—Medium large; ovate; acutely pointed; medium thickness; rugose.

*Length.*—About 5½ inches.

*Width.*—About 1⅜ inches.

*Color.*—Parsley Green, Plate 00962, page 193, Vol. 2 (HCG).

*Margin.*—Glandular; finely serrate.

*Petiole.*—Medium long; medium thickness.

*Glands.*—Average 2 in number; opposite; small; globose; oval; free.

Flowers: Medium late in comparison with other varieties; medium small.

*Color.*—Pale Pink, Key 2.5 R 9/3 (M).

*Date of first bloom.*—About Apr. 10.

*Date of full bloom.*—About Apr. 20.

Fruit:

*Maturity when described.*—Eating ripe (about Aug. 20).

*Size.*—Uniform; medium large.

*Axial diameter.*—2¾ inches.

*Transverse diameter in suture plane.*—2⅝ inches.

*Diameter at right angles to suture plane.*—2⅝ inches.

*Form.*—Uniform; symmetrical; broadly ovoid.

*Suture.*—Distinct; extends from base to, but discontinues at apex; has slight depression beyond pistil point.

*Ventral surface.*—Slightly lipped throughout left side.

*Cavity.*—Abrupt, with suture showing on one side.

*Base.*—Slightly truncate; oblique.

*Apex.*—Short; rounded; pistil point apical.

*Stem.*—Stout; about ⅛ inch long; glabrous; medium adherence to stone.

*Skin.*—Medium thickness; medium toughness; astringent; tenacious to flesh; no tendency to break in wet or dry seasons.

*Color.*—Highly blushed with Oxblood Red, Plate 00823/2, page 191, Vol. 2 (HCG).

*Down.*—Moderate; short; does not roll up when rubbed.

*Flesh.*—

*Color.*—Saffron Yellow, Plate 7/2, page 7, Vol. 1 (HCG), streaked with red next to stone.

*Surface of pit cavity.*—Porcelain Rose, Plate 620/1, page 147, Vol. 2 (HCG).

*Amygdalin.*—Wanting.

*Juice.*—Moderate quantity; rich.

*Texture.*—Fairly firm.

*Fibres.*—Abundant; medium fine; tender.

*Ripens.*—Fairly evenly.

*Flavor.*—Mild.

*Aroma.*—Distinct.

*Eating quality.*—Good.

*Stone.*—Free.

*Fibres.*—Part from flesh smoothly.

*Size.*—Medium small. *Length.*—1⅜ inches. *Thickness.*—¾ inch.

*Form.*—Obovoid; cuneate toward base.

*Base.*—Oblique.

*Hilum.*—Narrow; oval.

*Apex.*—Acute.

*Sides.*—Equal; curved on right and left sides.

*Surface.*—Regularly furrowed throughout; pitted from base to center.

*Ridges.*—Rounded.

*Pits.*—Elongated.

*Ventral edge.*—Thin; without wing.

*Dorsal edge.*—With deep, narrow groove throughout.

*Ridges on either side.*—Interrupted.

Use: Market; dessert; canning.

Keeping quality: Medium.

Shipping quality: Good.

I claim:

A new and distinct variety of peach tree of the yellow-fleshed, freestone, fruit-bearing type, substantially as herein shown and described, characterized particularly as to novelty by the unique combination of a hardy tree and flower bud habit, a fruit ripening season about the same as the Gleason strain of "Early Elberta" (unpatented), but the fruit skin being a much deeper red color which develops about a week before maturity to enable earlier harvesting and shipping, a deeper yellow fruit flesh color, and a richer and sweeter fruit flavor.

No references cited.

ROBERT E. BAGWILL, Primary Examiner